(12) United States Patent
Miyagawa et al.

(10) Patent No.: US 7,838,565 B2
(45) Date of Patent: Nov. 23, 2010

(54) USE OF CYCLOHEXENONE DERIVATIVES IN THE MANUFACTURE OF A MEDICAMENT FOR TREATING DIABETIC COMPLICATIONS

(75) Inventors: Masao Miyagawa, Tottori (JP); Takeshi Watanabe, Tottori (JP); Motoaki Saito, Tottori (JP); Bang Luu, Strasbourg (FR); Masashi Yamada, Tokyo (JP); Hiroto Suzuki, Tokyo (JP)

(73) Assignee: Meiji Dairies Corporation, Tokyo (JP)

( * ) Notice: Subject to any disclaimer, the term of this patent is extended or adjusted under 35 U.S.C. 154(b) by 1587 days.

(21) Appl. No.: 10/467,063

(22) PCT Filed: Feb. 15, 2002

(86) PCT No.: PCT/JP02/01291

§ 371 (c)(1),
(2), (4) Date: Dec. 31, 2003

(87) PCT Pub. No.: WO02/066023

PCT Pub. Date: Aug. 29, 2002

(65) Prior Publication Data

US 2004/0102527 A1 May 27, 2004

(30) Foreign Application Priority Data

Feb. 19, 2001 (JP) .............................. 2001-041586

(51) Int. Cl.
*A61K 31/12* (2006.01)
*A01N 35/00* (2006.01)
(52) U.S. Cl. ..................................................... 514/690
(58) Field of Classification Search .................. 514/690
See application file for complete search history.

(56) References Cited

U.S. PATENT DOCUMENTS

| 6,906,107 | B2 * | 6/2005 | Miyagawa et al. | .......... 514/690 |
| 2004/0115810 | A1 * | 6/2004 | Luu et al. | .................... 435/441 |
| 2004/0152786 | A1 * | 8/2004 | Luu et al. | .................... 514/690 |

FOREIGN PATENT DOCUMENTS

| EP | 0 555 149 | | 8/1993 |
| WO | WO98/56426 | * | 12/1998 |
| WO | WO99/08987 | * | 2/1999 |
| WO | 00 47199 | | 8/2000 |

OTHER PUBLICATIONS

Tarone et al. "Integrin function and regulation in development." International Journal of Developmental Biology. 2000. 44. pp. 725-731.*
Apfel, SC. "Neurotrophic Factors in the Therapy of Diabetic Neuropathy". American Journal of Medicine. 1999. vol. 107, No. 2B. pp. 34S-42S.*
Chiarelli et al. "Role of Growth Factors in the Development of Diabetic Complications". Hormone Research. 2000. vol. 53. pp. 53-67.*
Hammes et al. "Nerve Growth Factor Prevents Both Neuroretinal Programmed Cell Death and Capillary Pathology in Experimental Diabetes". Molecular Medicine. 1995. vol. 1, No. 5. pp. 527-534.*
Ahmed (Diabetes Research and Clinical Practice 67 (2005) 3-21).*
Takano et al (Neuroscience Letters, vol. 275, Issue 3 (1999) pp. 175-178).*
Biessels et al (Diabetologia (1994) 37:643-650).*
Zhuang et al (Experimental Neurology, vol. 140, Issue 2, (1996) 198-205).*
U.S. Appl. No. 10/468,138, filed Aug. 18, 2003, Miyagawa, et al.
Database Biosis 'Online! Biosciences Information Service, Philadelphia, PA, US; 1998 Unger J W et al: "Nerve growth factor (NGF) and diabetic neuropathy in the rat: Morphological investigations of the sural nerve, dorsal root ganglion, and spinal cord" Database accession No. PREV199800499846 XP002201770 abstract & Experimental Neurology, vol. 153, No. 1, 1998, pp. 23-34, ISSN: 0014-4886.
Database Biosis 'Online! Biosciences Information Service, Philadelphia, PA. US; 1995 Hammes Hans-Petet et al: "Nerve growth factor prevents both neuroretinal programmed cell death and capillary pathology in experimental diabetes." Database accession No. PREV199699149925 XP002201771 abstract & Molecular Medicine (Cambridge) vol. 1, No. 5, 1995, pp. 527-534, ISSN:1076-1551.
Database Biosis 'Online! Biosciences Information Service, Philadelphia, PA, US; Aug. 30, 1999 Apfel Stuart C: "Neurotrophic factors in the therapy of diabetic neuropathy." Database accesion No. PREV199900487598 XP002201772 abstract & American Journal of Medicine, vol. 107, No. 2 Part B, Aug. 30, 1999, pp. 34S-42S, ISSN: 0002-9343.

(Continued)

*Primary Examiner*—Frederick Krass
*Assistant Examiner*—Benjamin Packard
(74) *Attorney, Agent, or Firm*—Oblon, Spivak, McClelland, Maier & Neustadt, L.L.P.

(57) ABSTRACT

A preventive and/or therapeutic agent for diabetes complications, which comprises as an effective ingredient a cyclohexenone long-chain alcoholic derivative represented by the following formula (1): wherein, $R^1$, $R^2$ and $R^3$ each independently represents a hydrogen atom or a methyl group and X represents a linear or branched $C_{10-28}$ alkylene or alkenylene group. The cyclohexenone long-chain alcoholic derivative of the present invention significantly suppresses a reduction in a peripheral nerve conduction rate and alleviates the hypofunction of the bladder so that it is useful as a preventive and/or therapeutic agent for diabetes complications, particularly, for diabetic neuropathy.

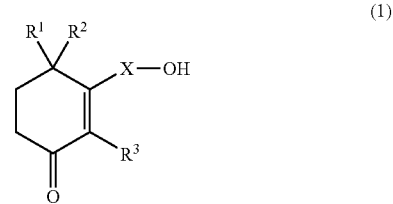

(1)

11 Claims, No Drawings

OTHER PUBLICATIONS

Database Biosis 'Online! Biosciences Information Service, Phladelphia, PA, US; 1984 Nishida T et al: "Uperoxide Dismutase EC-1.15.1.1 Activity in Diabetic Rat Retina" Database accession No. PREV198580008367 XP002201773 abstract & Japanese Journal of Ophthalmology, vol. 28, No. 4, 1984, pp. 377-382, ISSN: 0021-5155.

K.H. Gabbay N. Eng. J. Med.; vol. 288, pp. 831-836 1973.

U.S. Appl. No. 10/478,477, filed Nov. 21, 2003, Luu et al.

U.S. Appl. No. 10/550,305, filed Sep. 22, 2006, Luu, et al.

* cited by examiner

USE OF CYCLOHEXENONE DERIVATIVES IN THE MANUFACTURE OF A MEDICAMENT FOR TREATING DIABETIC COMPLICATIONS

TECHNICAL FIELD

The present invention relates to a preventive and/or therapeutic agent for diabetic complications typified by diabetic neuropathy.

BACKGROUND ART

Diabetes is a complex disease caused by hyperglycemia. As its essential treatment, the blood sugar level is controlled, in most cases by injection of insulin. What is really troublesome for those suffering from diabetes is, however, the advance to diabetic complications. As diabetic complications, diabetic retinopathy, diabetic nephropathy, diabetic angiopathy and diabetic neuropathy are known. In order to prevent the onset of diabetic complications or to retard the advance of them, proper blood sugar control is necessary over a long period of time. It is known that the longer the suffering period, the higher the incidence of diabetic complications.

As one of the factors for causing such diabetic complications, mentioned is abnormal acceleration of a polyol metabolic pathway (K. H. Gabbay, N. Eng. J. Med., 288, 831 (1973)). The enzyme controlling this polyol metabolic pathway is aldose reductase (AR). An AR inhibitor is now used widely as a remedy for diabetic neuropathy. Diabetic complications occur not by one factor but by the tangle of various factors over a long period of time so that a medicament having mechanism of single action cannot be regarded as an absolute remedy.

An object of the present invention is therefore to provide a novel preventive and/or therapeutic agent for diabetic complications, particularly for diabetic neuropathy.

DISCLOSURE OF THE INVENTION

With the foregoing in view, the present inventors carried out an extensive investigation on low molecular compounds capable of protecting the function of the peripheral nerve from being damaged by diabetes. As a result, it has been found that long-chain alcohols having a cyclohexenone skeleton represented by the below-described formula (1) have excellent peripheral-nerve-function protecting action, leading to completion of the present invention.

In addition, the present invention is to provide a pharmaceutical composition for preventing and/or treating diabetic complications, which comprises the cyclohexenone long-chain alcoholic derivative and a pharmaceutically acceptable carrier.

Also, the present invention is to provide use of the cyclohexenone long-chain alcoholic derivative for the manufacture of a preventive and/or therapeutic agent for diabetic complications.

Further, the present invention is to provide a method for preventing and/or treating diabetic complications, which comprises administering the cyclohexenone long-chain alcoholic derivative.

BEST MODE FOR CARRYING OUT THE INVENTION

In the present invention, there is thus provided a remedy for diabetic complications, which comprises a cyclohexenone long-chain alcoholic derivative represented by the following formula (1):

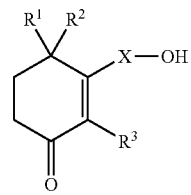

[wherein, $R^1$, $R^2$ and $R^3$ each independently represents a hydrogen atom or a methyl group and X represents a linear or branched $C_{10-28}$ alkylene or alkenylene group].

In the cyclohexenone long-chain alcoholic derivatives represented by the formula (1), X represents a linear or branched $C_{10-28}$ alkylene and alkenylene group. The branched alkylene or alkenylene group contains, as the side chain, a $C_{1-10}$ alkyl group. Examples of the alkyl group as the side chain include methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl and decyl groups. Among them, the methyl group is particularly preferred.

Substitution of the side chain to a linear alkylene or alkenylene group (which means an alkene structure having at least one carbon-carbon double bond) is preferably at the 3- and/or 7-position. As X, linear $C_{10-28}$ alkylene groups are preferred, with linear $C_{10-18}$ alkylene groups being particularly preferred.

$R^1$, $R^2$ and $R^3$ each independently represents a hydrogen atom or a methyl group. More preferably, at least one of them represents a methyl group.

The compound represented by the above-described formula (1) may exist as a pharmaceutically acceptable salt, or a solvate or hydrate thereof. The compound (1) has various isomers and these isomers are also embraced by the present invention.

The cyclohexenone long-chain alcoholic derivative represented by the formula (1) can be prepared, for example, in accordance with the following Process A or Process B.

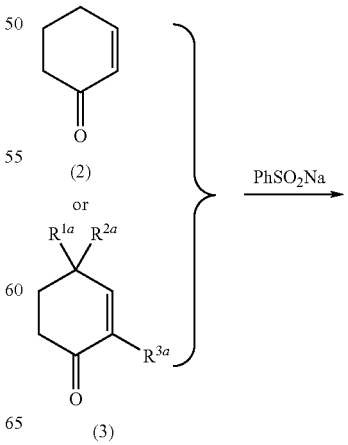

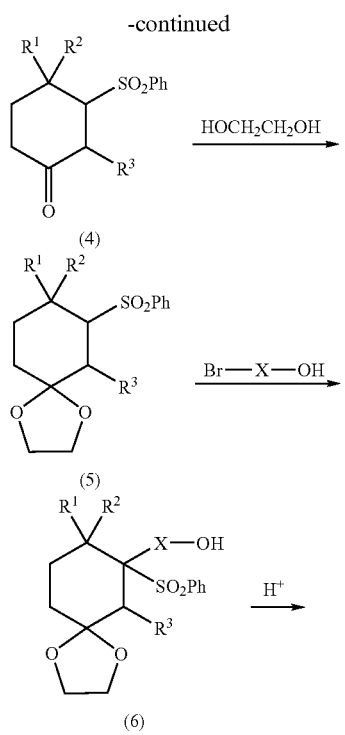

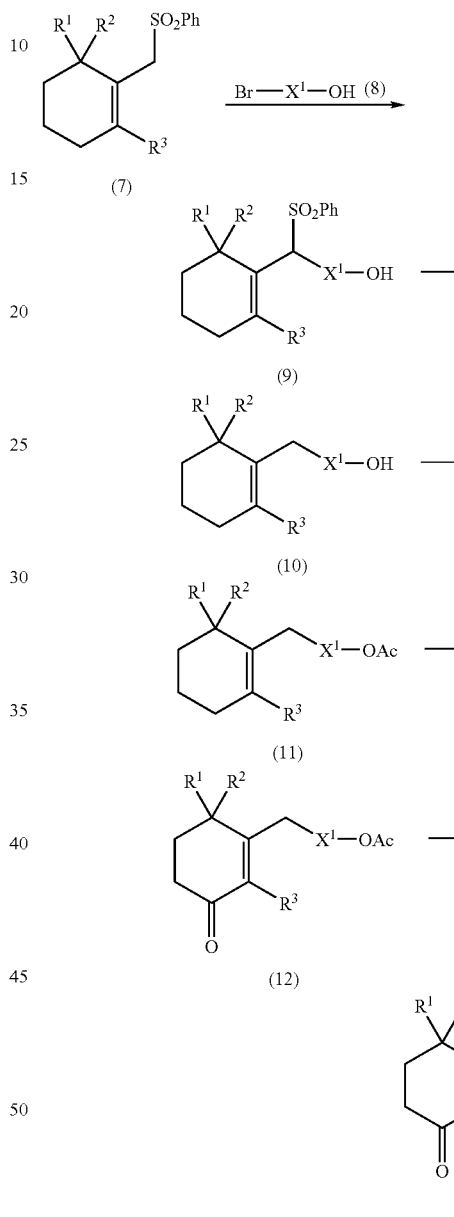

[wherein, $R^{1a}$, $R^{2a}$ and $R^{3a}$ each independently represents a hydrogen atom or a methyl group with the proviso that at least one of them represents a methyl group, Ph stands for a phenyl group and X, $R^1$, $R^2$ and $R^3$ have the same meanings as described above].

Described specifically, the compound (1) is available by reacting cyclohexenone (2) or methyl-substituted-2-cyclohexen-1-one (3) with a phenylsulfinic acid salt in the presence of an acid, reacting the resulting compound (4) with ethylene glycol, reacting the resulting ketal derivative (5) with a ω-halogenoalkanol or ω-halogenoalkenol, and subjecting the resulting compound (6) to acid treatment to eliminate the protective group.

The methyl-substituted-2-cyclohexen-1-one (3) used here as a raw material is available by reacting methyl-substituted cyclohexanone with a trialkylsilyl halide in the presence of butyl lithium, followed by oxidation in the presence of a palladium catalyst.

The reaction of cyclohexenone (2) or methyl-substituted-2-cyclohexen-1-one (3) with a phenylsulfinic acid salt, for example, sodium phenylsulfinate is preferably effected in the presence of an acid such as hydrochloric acid, sulfuric acid or phosphoric acid at 0 to 100° C. for 5 to 40 hours.

As the ω-halogenoalkanol to be reacted with the ketal derivative (5), a ω-bromoalkanol is preferred. The reaction between the ketal derivative (5) with the ω-halogenoalkanol is preferably effected in the presence of a metal compound such as butyl lithium under low temperature conditions.

The elimination of the phenylsulfonyl and ketal-protective groups from the compound (6) so obtained is preferably effected by reacting it with an acid such as paratoluenesulfonic acid.

[wherein, $X^1$ represents a $C_{9\text{-}27}$ alkylene or alkenylene group, Ac stands for an acyl group and $R^1$, $R^2$, $R^3$ and Ph have the same meanings as described above].

Described specifically, the compound (1a) can be obtained by reacting the compound (7) [available in accordance with, for example, Tetrahedron, 52, 14891-14904(1996)] with ω-bromoalcohol (8), eliminating the phenylsulfonyl group from the resulting compound (9), protecting the hydroxy group of the resulting compound (10), oxidizing the resulting compound (11), and then eliminating the hydroxy-protecting group from the resulting compound (12).

The reaction of the compound (7) with the ω-bromoalcohol (8) is preferably conducted in the presence of a metal compound such as butyl lithium under low temperature conditions.

The phenylsulfonyl group is eliminated from the compound (9), for example, by reacting the compound with a phosphate salt in the presence of sodium amalgam.

As the hydroxy-protecting group of the compound (10), an acetyl group is preferred. The protection reaction is conducted, for example, by reacting the compound (10) with acetic anhydride.

The compound (11) is oxidized by reacting it with an alkyl hydroperoxide such as t-butyl hydroperoxide in the presence of a metal compound such as ruthenium trichloride.

The deprotection of the compound (12) is preferably conducted by hydrolyzing it in the presence of a base such as potassium carbonate.

The cyclohexenone long-chain alcoholic derivatives (1) thus obtained significantly suppress lowering in a stimulus conduction rate of the peripheral nerve in animal models of diabetes, thereby significantly alleviating hypofunction of the urinary bladder such as dysuria as will be described later in test, so that they are useful as a preventive and/or therapeutic agent for diabetic complications, particularly diabetic neuropathy, in mammals including human.

The cyclohexenone long-chain alcoholic derivatives (1) of the present invention are low molecular compounds so that they can be administered either orally or parenterally (intramuscularly, subcutaneously, intravenously or by way of suppository).

Oral preparations can be formulated into tablets, covered tablets, coated tablets, granules, capsules, solutions, syrups, elixirs, or oil or aqueous suspensions in a manner known per se in the art after addition of an excipient and if necessary a binder, a disintegrator, a lubricant, a colorant and/or a corrigent. Examples of the excipient include lactose, corn starch, saccharose, glucose, sorbitol and crystalline cellulose. Examples of the binder include polyvinyl alcohol, polyvinyl ether, ethyl cellulose, methyl cellulose, gum arabic, tragacanth, gelatin, shellac, hydroxypropyl cellulose, hydroxypropyl starch and polyvinyl pyrrolidone.

Examples of the disintegrator include starch, agar, gelatin powder, crystalline cellulose, calcium carbonate, sodium bicarbonate, calcium citrate, dextran and pectin; those of the lubricant include magnesium stearate, talc, polyethylene glycol, silica and hardened vegetable oil. As the colorant, pharmaceutically acceptable ones as an additive can be used. Examples of the corrigent include cocoa powder, menthol, aromatic acid, peppermint oil, camphor and cinnamon powder. The tablet can also be used in the form of a coated tablet available by applying sugar coating, gelatin coating or the like to granules as needed.

Injections, more specifically, subcutaneous, intramuscular or intravenous injections are formulated in a manner known per se in the art by adding a pH regulator, buffer, stabilizer and/or preservative as needed. It is also possible to fill the injection solution in a vial or the like and lyophilize it into a solid preparation which is reconstituted immediately before use. One dose is filled in a vial or alternatively, multiple doses are filled in one vial.

For a human adult, the dose of the invention compound as a medicament usually falls within a range of from 0.01 to 1000 mg/day, with a range of from 0.1 to 100 mg/day being preferred. This daily dose is administered once a day or in 2 to 4 portions a day.

EXAMPLES

The present invention will hereinafter be described more specifically by Examples.

Preparation Example 1

(1) To a 20 ml THF solution of 7 ml of N,N-diisopropylamine, 35.4 ml of a 1.4M n-butyl lithium solution was added dropwise at −78° C., followed by stirring at 0° C. for 30 minutes. The resulting diisopropyl aminolithium (LDA) solution was then added dropwise to a 10 ml THF solution of 4 ml of 4-methylcyclohexan-1-one at −78° C. After stirring at −78° C. for 1 hour, 6.5 ml of trimethylsilyl chloride was added dropwise. After stirring at room temperature for 1 hour, the reaction mixture was poured into an aqueous sodium bicarbonate solution. The resulting mixture was extracted with ether. The organic layer was washed with saturated saline, dried over magnesium sulfate and distilled under reduced pressure to remove the solvent. Distillation under reduced pressure yielded 5.83 g of 4-methyl-1-(trimethylsilyloxy)-1-cyclohexene (yield: 96%).

4-Methyl-1-(trimethylsilyloxy)-1-cyclohexene

Molecular weight: 184 ($C_{10}H_{20}OSi$)

TLC: (hexane:ethyl acetate=8:2) Rf=0.8

$^1$H-NMR (200 MHz, CDCl$_3$) δ: 0.17(s,9H,Si—(CH$_3$)$_3$), 0.94 (d,J=6.2Hz,3H,H-7), 1.2-1.43(m,1H,H-4), 1.57-1.76(m, 3H,H-3,6), 1.88-2.14(m,3H,H-5), 4.8-4.83(m,1H,H-2).

$^{13}$C-NMR (50 MHz, CDCl$_3$) δ: 0.3(Si—(CH$_3$)$_3$), 21.2(C-7), 28.3(C-4), 29.6(C-5), 31.3(C-6), 32.3(C-3), 103.5(C-2), 150.1(C-1).

IR(NaCl): 3052, 3021, 2954, 2926, 1670, 1457, 1371, 1252, 1190, 1046, 892, 844.

(2) A catalytic amount of palladium acetate was added to a 70 ml dimethylsulfoxide (DMSO) solution of 3.53 g of 4-methyl-1-(trimethylsilyloxy)-1-cyclohexane, followed by stirring while introducing oxygen for 6 hours. After the addition of water at 0° C., the reaction mixture was filtered and then extracted with ether. The solvent was distilled off from the organic layer under reduced pressure. The residue was dissolved in hexane-water to extract with hexane. The hexane layer was washed with saturated saline and dried over magnesium sulfate. The solvent was distilled off under reduced pressure, whereby 4-methyl-2-cyclohexen-1-one was obtained in the form of an oil (yield: 72%).

4-Methyl-2-cyclohexen-1-one

Molecular weight: 110 ($C_7H_{10}O$)

TLC: (hexane:ethyl acetate=8:2) Rf=0.35

$^1$H-NMR (200 MHz, CDCl$_3$) δ: 1.15 (d,J=7.1 Hz,3H,H-7), 1.56-1.76(m,1H,H-5a), 2.1(dqa,J$_{gem}$=13.3 Hz,$^3$J=4.9 Hz,1H,H-5e), 2.26-2.48(m,2H,H-6), 2.49-2.62(m,1H,H-4), 5.94(dd, $^3$J=10.1 Hz, $^4$J=2.5 Hz,1H, H-2), 6.79 (ddd, $^3$J=10.1 Hz, $^3$J=2.7 Hz, $^4$J=1.5 Hz, 1H, H-3).

$^{13}$C-NMR (50 MHz, CDCl$_3$) δ: 20.1(C-7), 29.6(C-5), 30.9 (C-4), 36.8(C-6), 128.4(C-2), 156.2(C-3), 199.7(C-1).

IR(NaCl): 3025, 2958, 2932, 1683, 1617, 1458, 1391, 1375, 1251, 1094, 1053, 1016, 828, 750.

(3) Sodium benzenesulfinate (3.0 g) was added to a solution containing 1.52 g of 4-methyl-2-cyclohexen-1-one and 9 ml of water. 1N Hydrochloric acid (18 ml) was added dropwise to the resulting solution. After stirring at room temperature for 24 hours, the crystals so precipitated were filtered and washed with water, isopropanol and cold ether. After recrystallization from isopropanol, 4-methyl-3-(phenylsulfonyl)-cyclohexan-1-one was obtained in the form of white crystals (yield: 72%).

4-Methyl-3-(phenylsulfonyl)-cyclohexan-1-one

Molecular weight: 252 ($C_{13}H_{16}O_3S$)

Melting point: 71 to 74° C.

TLC: (hexane:ethyl acetate=6:4) Rf=0.2

$^1$H-NMR (200MHz, $CDCl_3$), -trans δ: 1.32(d,J=6.9 Hz, 3H,H-7), 1.5-1.7(m,1H,H-5), 2.15-2.3 (m,1H,H-5), 2.35-2.5(m,3H,H-4,6), 2.55-2.68(m,2H,H-2), 3.17(ddd,J=8 Hz,J=6.6 Hz,J=6.4 Hz,1H,H-3), 7.52-7.72(m,3H,H ar.-3', 4'), 7.83-7.9(m,2H,H ar.-2'), -cis δ: 1.44(d,J=7.1 Hz,3H,H-7), 1.75-1.9(m,1H, H-5), 1.95-2.1 (m,1H,H-5), 2.23-2.5 (m,3H,H-4,6), 2.73-2.9(m,2H,H-2), 3.34(dt,J=12.9 Hz,J=4 Hz,1H,H-3), 7.52-7.72(m,3H,H ar.3',4'), 7.83-7.9 (m,2H,H ar.-2').

$^{13}$C-NMR (50 MHz, $CDCl_3$)

-trans δ: 20.3(C-7), 28.5(C-4), 30.4(C-5), 37.9(C-6 or -2), 38.6(C-2 or -6), 66.3(C-3), 128.6(C ar.-2' or -3'), 129.1 (C ar.-3' or -2'), 133.9 (C ar.-4'), 137.2 (C ar.-1'), 206.6(C-1).

-cis δ: 13(C-7), 27.2(C-4), 31.1(C-5), 35.9(C-6 or -2), 36.9 (C-2 or -6), 64.6(C-3), 128.3(C ar.-2' or -3'), 129.1(C ar.-3' or -2'), 133.9(C ar.-4'), 138(C ar.-l'), 206.6(C-1).

MS(EI): 111.1 (M-$SO_2$Ph,88), 110.1(27), 83, 15(32), 77.1 (29), 69.1(36), 55.2(100).

(4) To a solution of 2.45 g of 4-methyl-3-(phenylsulfonyl)-cyclohexan-1-one dissolved in 40 ml of benzene, were added 0.7 ml of 1,2-ethanediol and 0.2 g of paratoluenesulfonic anhydride. The resulting mixture was heated under reflux for 4 hours. After the reaction, a 2M aqueous sodium bicarbonate solution was added and the resulting mixture was extracted with ethyl acetate three times. The combined organic layers were washed with saturated saline, and dried over magnesium sulfate. The solvent was then distilled off under reduced pressure. The residue was recrystallized from ether, whereby 1,1-(ethylenedioxy)-4-methyl-3-(phenylsulfonyl)-cyclohexane was obtained in the form of white crystals (yield: 97%).

1,1-Ethylenedioxy-4-methyl-3-phenylsulfonyl-cyclohexane

Molecular weight: 296 ($C_{15}H_{20}O_4S$)

Melting point: 105 to 106° C.

TLC: (hexane:ethyl acetate=6:4) Rf=0.3

$^1$H-NMR (200 MHz, $CDCl_3$), -trans δ: 1.23(d,J=6.1 Hz,3H, H-7), 1.37-1.77(m,6H,H-2a,4,5,6), 1.84(ddd,$J_{gem}$=12.9 Hz,$^3$J=3.7 Hz, $^4$J=2.7 Hz,1H,H-2e), 3.02(ddd,$^3$J=13 Hz,$^3$J=10.3 Hz,$^3$J=3.7 Hz,1H,H-3), 3.71-3.91(m,4H,O—$CH_2$—$CH_2$—O), 7.48-7.67(m,3H H ar.-3',4'), 7.8-7.88(m, 2H,H ar.-2')

-cis δ: 1.18(d,J=6.9 Hz,3H,H-7), 1.37-1.77(m,4H,H-5,6), 1.84(ddd,$J_{gem}$=13 Hz,$^3$J=3.7 Hz,$^4$J=2.7 Hz,1H,H-2e), 2.02 (t,J=13 Hz,1H, H-2a), 2.30-2.45(m,1H,H-4), 3.29(dt, $^3$J=13 Hz, $^3$J=3.7 Hz,1H,H-3), 3.71-3.91(m,4H,O—$CH_2$—$CH_2$—O), 7.48-7.67(m,3H,H ar.-3',4'), 7.8-7.88(m, 2H,H ar.-2').

$^{13}$C-NMR (50 MHz,$CDCl_3$)

-trans δ: 20.4(C-7), 31.9(C-4), 32.6(C-5), 34.1(C-6), 35.8(C-2), 64.4($CH_2$—O), 66.8(C-3), 107.9(C-1), 128.6(C ar.-3' or -2'), 129 (C ar.-2' or -3'), 133.5(C ar.-4'), 138(C ar.-1').

-cis δ: 12.4(C-7), 26.7(C-4), 29.2(C-5,6), 32(C-2), 64.1(C-3), 64.4($CH_2$—O),108.2(C-1), 128.3(C ar.-2',3'), 133.5(C ar.-4'), 138.5(C ar.-1')

IR(KBr): 3060, 2968, 2938, 1583, 1448, 1301, 1267, 1158, 1144, 1082, 1023, 939, 916, 838, 749, 718, 689.

Elementary analysis (%):

Calculated: C; 60.79, H; 6.8

Found: C; 60.5, H: 6.9

(5) A solution of n-butyl lithium (1.8 ml) was added dropwise to a 5 ml THF solution of 560 mg of 1,1-(ethylenedioxy)-4-methyl-3-(phenylsulfonyl)-cyclohexane and 4 mg of triphenylmethane under an argon gas stream at –78° C. The resulting mixture was stirred for 10 minutes and then reacted at room temperature for one hour. HMPT (1 ml) was added and the resulting mixture was cooled to –78° C. again, followed by the dropwise addition of a 2 ml THF solution of 205 mg of 14-bromo-1-tetradecanol. After reaction at –20° C. for 2 hours, the reaction mixture was poured into a saturated solution of ammonium chloride. The resulting mixture was extracted with ether. The organic layer was washed with water and saturated saline, dried over magnesium sulfate and distilled under reduced pressure to remove the solvent. The residue was purified by chromatography on a silica gel column while using hexane-ethyl acetate, whereby 1,1-(ethylenedioxy)-3-(14-hydroxytetradecyl)-4-methyl-3-(phenylsulfonyl)-cyclohexane was obtained in the form of a colorless oil (yield: 98%).

1-1-(Ethylenedioxy)-3-(14-hydroxytetradecyl)-4-methyl-3-(phenylsulfonyl)-cyclohexane Molecular weight: 508 ($C_{29}H_{48}O_5S$)

TLC: (hexane:ethyl acetate=60:40) Rf=0.22

$^1$H-NMR (200 MHz) δ: 1.13(d,J=6 Hz,3H,H-21), 1.28(s large, 20H, H-9a H-18), 1.43-1.6(m,9H,H-4,5,7,8,19), 1.67(m,1H,H-2), 1.89(dd,$J_{gem}$=12.5 Hz,J=3 Hz,1H,H-6e), 2.14(t large, J=12.5 Hz,1H,H-6a), 2.43(dd,$J_{gem}$=13.8 Hz,$^4$J=2.5 Hz,1H,H-2), 3.63(t,J=6.5 Hz,2H,H-20), 3.83-3.97(m,4H,O—$CH_2$—$CH_2$—O), 7.49-7.68(m,3H,H ar.-3',4'), 7.80-7.88(m,2H,H ar.-2').

$^{13}$C-NMR (50 MHz) δ: 16.1(C-21), 24.4(C-18), 25.6(C-5 or -7), 25.8(C-7 or -5), 29.5(C-9 to C-17), 30.3(C-8), 32.7(C-19), 34.9(C-6), 35.5(C-4), 36.2(C-2), 62.8(C-20), 63.9 and 65.1(O—$CH_2$—$CH_2$—O), 7.12(C-3), 108.4(C-1), 128.7(C ar.-3'), 130.1 (C ar.-2'), 133.3(C ar.-4'), 136.8(C ar.-1')

IR(NaCl): 3510(m large, O—H), 3063(f,C—H), 2926, 2853 (f, C—H), 1585(f,C—C), 1447 (m), 1286, 1140(F,$SO_2$), 1096, 1083 (m,O—$CH_2$), 723, 693(m)

MS(Cl—$NH_3$): 526.4 ($MNH_4$, 16), 369.4 ($MH_2$—$SO_2$Ph, 28), 370.4(MH—$SO_2$Ph,25), 367.3(M—$SO_2$Ph,100), 311.3(7), 307.3(8), 305.3(9), 175(17), 159.9(11), 98.9(35), 94(6), 78(11).

Elementary analysis (%):

Calculated: C; 67.98, H; 9.37

Found: C; 67.4, H; 9.1

(6) Paratoluenesulfonic acid (20 mg) was added to a solution of 235 mg of 1,1-(ethylenedioxy)-3-(14-hydroxytetradecyl)-4-methyl-3-(phenylsulfonyl)-cyclohexane in 20 ml of chloroform and 4 ml of acetone. The resulting mixture was reacted at 50° C. for 24 hours. To the reaction mixture was added 10 ml of a saturated aqueous solution of sodium bicarbonate, followed by extraction with dichloromethane. The organic layer was washed with saturated saline, dried over magnesium sulfate and distilled under reduced pressure to remove the solvent. The residue was purified by chromatography on a silica gel column while using hexane-ethyl acetate, whereby 3-(14-hydroxytetradecyl)-4-methyl-2-cyclohexen-1-one was obtained in the form of a colorless oil (yield: 75%).

3-(14-Hydroxytetradecyl)-4-methyl-2-cyclohexen-1-one

Molecular weight: 322 ($C_{21}H_{38}O_2$)

TLC: (hexane:ethyl acetate=6:4) Rf=0.3

MS (EI): 322.2 ($M^+$,37), 304.1(M-$H_2$O,12), 292.1(21), 164.9 ($C_{11}H_{17}$O,9), 151($C_{10}H_{15}O$,4), 138.1(12), 137($C_9H_{13}$O, 43), 96(30), 94.9(24), 81(24), 78.9(13), 69(15), 67(25), 55(37).

Elementary analysis (%)
Calculated: C; 78.20, H; 11.88
Found: C; 78.6, H; 11.9

Preparation Example 2

In a similar manner to Preparation Example 1, 3-(15-hydroxypentadecyl)-4-methyl-2-cyclohexen-1-one (Compound 2) was synthesized.

Preparation Example 3

To a methanol solution (8 ml) containing 132 mg (0.36 mmol, 1 equivalent) of 3-(12-acetoxypentadecyl)-2,4,4-trimethyl-2-cyclohexen-1-one were added 3 drops of water and 74 mg (0.54 mmol, 1.5 equivalents) of $K_2CO_3$. The resulting mixture was stirred at room temperature for 2.5 hours. After adjustment to pH 7 with 5% HCl, the reaction mixture was extracted with ether, dried over magnesium sulfate and distilled under reduced pressure to remove the solvent. The residue was purified by chromatography on a silica gel column, followed by elution with hexane-ethyl acetate (8:2 to 7:3), whereby 94 mg (yield: 81%) of 3-(12hydroxydodecyl)-2,4,4-trimethyl-2-cyclohexen-1-one (Compound 3) was obtained in the form of a colorless oil.

3-(12-Hydroxydodecyl)-2,4,4-trimethyl-2-cyclohexen-1-one
TLC: (hexane:ethyl acetate=7:3) Rf=0.2
GC: 40 to 280° C. (20° C./min) 12 min, 99%
$^1$H-NMR (200 MHz) δ: 1.13 (ds,6H,H-19,20), 1.26(s,br,16H, H-9 to H-16), 1.35-1.69(m,4H,H-8,17), 1.73(s,3H,H-21), 1.77(t,J=7.5 Hz,2H,H-5), 2.11-2.19(m,2H,H-7), 2.43(t, J=6.8 Hz,2H,H-6), 3.61(t,J=6.8 Hz,2H,H-18).
$^{13}$C-NMR (50 MHz) δ: 11.4(C-21), 25.7(C-16), 26.8(C-19, 20), 28.8(C-8), 29.5(C-9 to C-15), 30.45(C-7), 32.7(C-17), 34.2(C-5), 36.2(C-4), 37.3(C-6), 62.9(C-18), 130.4(C-2), 165.4(C-3), 199(C-1).
IRv: 3440 (broad OH), 2925, 2852(w,C—H), 1666(w, C=O), 1605(s,C=C), 1467(s,C—H).

Preparation Example 4

In a similar manner to Preparation Example 3, the below-described compound was obtained. The numeral in parentheses indicates the Rf value of TLC with a 7:3 mixed eluent of hexane and ethyl acetate.
(1) 3-(15-Hydroxypentadecyl)-2,4,4-trimethyl-2-cyclohexen1-one (Compound 4) (Rf=0.29)
(2) 3-(18-Hydroxyoctadecyl)-2,4,4-trimethyl-2-cyclohexen-1-one (Compound 5) (Rf=0.25)

Test 1 (Neural Stimulus Conduction Rate)

To a rat, 65 mg/kg of streptozotocin (STZ) was administered intraperitoneally to prepare a model rat of diabetes. After intraperitoneal administration of Compound 4 obtained in Preparation Example 4 at a daily dose of 8 mg/kg for 8 weeks from two days after administration of STZ, the conduction rate of stimulus to sciatic nerve was measured by inserting a needle electrode for potential measurement into the vicinity of the right sciatic nerve, right Achilles tendon, and right plantar. Measurement was conducted three times and the mean of them was designated as the nerve stimulus conduction rate of the rat. Each group consisted of 10 to 12 rats.

As a result, as shown in Table 1, the conduction rate was 49.4 m/sec on average in a diabetes-free rat group, while it was 42.4 m/sec on average in an administration-free group of diabetes rats, showing lowering in a nerve stimulus conduction rate in the latter group. In the Compound-4-administered group, on the other hand, the rate was 45.5 m/sec on average, showing that administration significantly suppressed the lowering in a nerve stimulus conduction rate resulting from diabetes.

TABLE 1

|  | Diabetes-free rat group (control) | Diabetes rat group | (mean ± S.E.) Compound-administered group |
|---|---|---|---|
| Conduction rate of stimulus to nerve (m/sec) | 49.4 ± 1.8 | 42.4 ± 0.5* | 45.5 ± 1.2** |

*$p < 0.05$ relative to the control group
**$p < 0.05$ relative to the diabetes rat group Test 2 (Maximum Quantity Excreted by Single Urination)

In a similar manner to Test 1, Compound 4 obtained in Preparation Example 4 was administered intraperitoneally to a rat at a daily dose of 8 mg/kg day for 8 weeks from two days after administration of STZ. Its urination pattern such as urination frequency and urination amount was then recorded for 24 hours at 2.5-min intervals by using a metabolic cage.

As a result, as shown in Table 2, the maximum quantity excreted by single urination was 4.89±0.38 ml in the administration-free diabetes rat group, while that of the Compound-4-administered rat group was 3.71±0.26 ml, showing a significant decrease in the quantity. Thus, it has been found that administration brought about an improvement.

TABLE 2

|  | Diabetes-free rat group (control) | Diabetes rat group | (mean ± S.E.) Administered group |
|---|---|---|---|
| Maximum amount excreted by single urination (ml) | 1.47 ± 0.10 | 4.89 ± 0.38* | 3.71 ± 0.26** |

*$p < 0.05$ relative to the control group
**$p < 0.05$ relative to the diabetes rat group Test 3 (Bladder Capacity and Urination Efficiency)

In a similar manner to Test 1, Compound 4 obtained in Preparation Example 4 was administered intraperitoneally to a rat at a daily dose of 8 mg/kg for 8 weeks from two days after administration of STZ. The intravesical pressure of the rat was then measured under anesthesia, whereby bladder capacity and urination efficiency were determined.

As a result, as shown in Table 3, the urination-inducing bladder capacity of a diabetes-free rat group was 0.25±0.03 ml, while that of an administration-free diabetes rat group was 0.90±0.14 ml, showing a deterioration in the bladder function. That of a Compound-4-administered diabetes rat group was, on the other hand, 0.54±0.07 ml, showing a significant improvement compared with the administration-free group.

The urination efficiency was determined from an excreted quantity/bladder capacity ratio. The diabetes-free rat group exhibited a urination efficiency of 87.5±2.2%, while the-administration-free diabetes rat group exhibited 53.6±6.5%, showing a reduction in the efficiency. The Compound-4-administered diabetes rat group, on the other hand, exhibited 75.0±6.1%, showing a significant improvement compared with the administration-free group.

TABLE 3

|  | Diabetes-free rat group (control) | Diabetes rat group | (mean ± S.E.) Test-compound-administered group |
|---|---|---|---|
| Bladder capacity (ml) | 0.25 ± 0.03 | 0.90 ± 0.14* | 0.54 ± 0.07** |
| Urination efficiency (%) | 87.5 ± 2.2 | 53.6 ± 6.5* | 75.0 ± 6.1** |

*p < 0.05 relative to the control group
**p < 0.05 relative to the diabetes rat group Urination efficiency (%)=100×excreted quantity/bladder capacity

INDUSTRIAL APPLICABILITY

The cyclohexenone long-chain alcoholic derivatives according to the present invention significantly suppress a reduction in a peripheral nerve conduction rate in the animal models of diabetes and alleviate a hypofunction of the bladder so that it is useful as a remedy for diabetes complications, particularly, for diabetes neuropathy.

The invention claimed is:

1. A method for treating diabetic complications, comprising:
    administering to a diabetic patient suffering from lowering in a stimulus conduction rate of a peripheral nerve an effective amount of a composition comprising:
    a cyclohexenone long-chain alcoholic compound represented by the following formula (1):

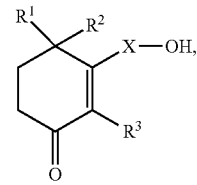

(1)

wherein
    $R^1$, $R^2$ and $R^3$ each independently represent a hydrogen atom or a methyl group, and
    X represents a linear or branched $C_{10-28}$ alkylene group;
or a salt of the compound of formula (1), wherein the diabetic complications are induced by the lowering in a stimulus conduction rate of a peripheral nerve, and wherein said diabetic complications comprise diabetic neuropathy.

2. The method of claim 1, wherein a dosage of the compound of formula (1) ranging from 0.01 to 1,000 mg per day is administered to a human subject.

3. The method of claim 1, wherein $R^1$, $R^2$ and $R^3$ are hydrogen.

4. The method of claim 1, wherein at least one of $R^1$, $R^2$ and $R^3$ is a methyl group.

5. The method of claim 1, wherein at least two of $R^1$, $R^2$ and $R^3$ are methyl groups.

6. The method of claim 1, wherein $R^1$, $R^2$ and $R^3$ are methyl groups.

7. The method of claim 1, wherein X represents a linear $C_{10-28}$ alkylene group.

8. The method of claim 1, wherein X represents a branched $C_{10-28}$ alkylene group.

9. The method of claim 1, wherein at least one of $R^1$, $R^2$ or $R^3$ is a methyl group and X is a linear $C_{10}$-$C_{18}$ alkylene group in the compound of formula (1).

10. The method of claim 1, wherein said compound is administered orally.

11. The method of claim 1, wherein said compound is administered parenterally.

* * * * *